United States Patent [19]

Fischer et al.

[11] Patent Number: 4,851,352

[45] Date of Patent: Jul. 25, 1989

[54] SOLVENT COMPOSITION FOR THE DETERMINATION OF WATER BY THE KARL FISCHER METHOD

[75] Inventors: Wolfgang Fischer; Edda Arlt; Karl D. Krenn, all of Darmstadt, Fed. Rep. of Germany

[73] Assignee: Merck Patent Gesellschaft Mit Beschrankter Haftung, Darmstadt, Fed. Rep. of Germany

[21] Appl. No.: 873,919

[22] Filed: Jun. 13, 1986

[30] Foreign Application Priority Data

Jun. 15, 1985 [DE]  Fed. Rep. of Germany ....... 3521544

[51] Int. Cl.$^4$ ............................................ G01N 33/18
[52] U.S. Cl. ..................................... 436/42; 252/364; 436/17; 436/18
[58] Field of Search ....................... 436/42, 39, 17, 18, 436/126; 252/364; 204/1 T

[56] References Cited

U.S. PATENT DOCUMENTS

| | | | |
|---|---|---|---|
| 4,185,964 | 1/1980 | Lancaster | 436/18 |
| 4,416,997 | 11/1983 | Fischer et al. | 436/42 |
| 4,485,175 | 11/1984 | Ledis et al. | 436/63 |
| 4,521,518 | 6/1985 | Carter et al. | 436/10 |
| 4,528,274 | 7/1985 | Carter et al. | 436/10 |
| 4,550,083 | 10/1985 | Fischer et al. | 436/42 |
| 4,605,784 | 8/1986 | Eubanks et al. | 568/614 |
| 4,619,900 | 10/1986 | Scholz | 436/42 |

FOREIGN PATENT DOCUMENTS 82860  5/1985  Japan ..................................... 436/42

OTHER PUBLICATIONS

Pittsburgh Conference Abstracts No. 1156 (1985).

*Primary Examiner*—Barry S. Richman
*Assistant Examiner*—Timothy M. McMahon
*Attorney, Agent, or Firm*—Millen, White & Zelano

[57] ABSTRACT

A solvent composition useful for the determination of water by the Karl Fischer method, comprises an ethylene glycol monoalkyl ether and a tetraalkylated ammonium salt.

26 Claims, No Drawings

4,851,352

SOLVENT COMPOSITION FOR THE DETERMINATION OF WATER BY THE KARL FISCHER METHOD

BACKGROUND OF THE INVENTION

The invention relates to a solvent composition useful in the determination of the amount of water by the Karl Fischer method, and to a method of use of the solvent composition in the determination of the amount of water.

DESCRIPTION OF THE PRIOR ART

The determination of water by the Karl Fischer method has been known for a long time (Angew. Chemie 48, 394 (1935)). The procedure for this method involves a solvent being initially introduced and titrated with Karl Fischer solution to the end point to remove the water content. Then a defined amount of the sample which is to be investigated is dissolved in the solvent and titrated with the Karl Fischer solution until reaching the color change. The water content is then calculated from the quantity of sample, the amount of Karl Fischer solution consumed, and the factor for the solution; such calculation procedures are known in the art.

The solvents which are generally used are alcohols, especially methanol. Examples of others which are customary are pyridine, ethylene glycol monomethyl ether, chloroform, dimethyl sulfoxide, formamide, dimethylforamide and others. The solvents are used either alone or as mixtures, in order either to improve the solvent properties for certain groups of substances or to suppress the presence of interfering side reactions.

However, interfering side reactions can occur, particularly in the determination of water present in ketones and aldehydes. If methanol or another alcohol is used as a solvent for these analyses, then the determined figures for water are higher than the actual value, because of the formation of acetal or ketal. When pyridine is used, the sulfur dioxide contained in the Karl Fischer reagent causes bisulfite additions onto the carbonyl group, with the result that water is consumed, and thus too low a value is registered. It may be the case that as a consequence of the side reactions which have been described, the formation of water and the consumption of water partly compensate, and thus it is no longer possible to obtain reliable analytical figures.

Attempts have been made to avoid these interfering side reactions by the use of halogenated alcohols as solvent (German Offenlegungsschrift No. 3,329,020). Our own experiments with these solvents have shown that although by using them the formation of water is satisfactorily suppressed, they tend to increase the additional consumption of water, i.e., because of the bisulfite addition, the figure for water which is determined is frequently too low.

It is disclosed in *Pittsburgh Conference Abstracts No. 1156*, (1985), that ethylene glycol monomethyl ether is unsuitable for the determination of water in aldehydes and ketones because of the formation of acetals and ketals, respectively.

SUMMARY OF THE INVENTION

It is an object of this invention to provide an improved solvent which ameliorates or overcomes these problems.

Upon further study of the specification and appended claims, further objects and advantages of this invention will become apparent to those skilled in the art.

In a composition aspect, the invention comprises a solvent composition for the determination of water by the Karl Fischer method, the improvement comprising a composition of ethylene glycol monoalkyl ethers and certain ammonium salts. The solvent is particularly suitable for the problematic determination of the amount of water in aldehydes and ketones.

The invention furthermore relates, in a method of use aspect, to a method for the determination of water by the Karl Fischer method using the aforementioned solvent composition.

DETAILED DISCUSSION

Suitable ethylene glycol monoalkyl ethers are preferably those having an alkyl group containing 1–8 carbon atoms, particularly ethylene glycol monomethyl and monoethyl ether. Corresponding derivatives of the diethylene and triethylene glycol monoalkyl ethers are also suitable, for example, diethylene glycol monomethyl ether, etc.

Suitable tetraalkylated ammonium salts are those having alkyl groups containing 1–6 carbon atoms, it being possible for the alkyl groups to be either all the same length or different lengths; preferably tetramethylammonium, tetraethylammonium and tetrapropylammonium salts are used, most preferably the tetraethylammonium salt. All anions which do not interfere with the determination of water by the Karl Fischer method are suitable to form salts, such as halides, sulfates, nitrates, acetates, thiocyanates, and the like; preferably the halides, such as fluoride, chloride, bromide and iodide, particularly the appropriate bromides. Tetraethylammonium bromide is the most preferred salt.

The solvent composition of the invention contains about 0.01 to 1 mole of the tetraalkylammonium salt per liter, of ethylene glycol monoalkyl ether or other ether, preferably 0.1 to 0.8 mol/l, in particular, about 0.5 mol/l. The upper limit of the range is determined, in particular, by the solubility of the particular salt.

As an example of preparation of the solvent composition, e.g., 0.5 mol of a tetraalkylammonium salt is simply dissolved in one liter of ethylene glycol monoalkyl ether, with stirring.

For the determination of water, the solvent composition of the invention, in which the sample which is to be determined is to be dissolved, is first titrated to the end point, the sample is then added, and titration with a conventional Karl Fischer reagent is again carried out to the color change. A conventional Karl Fischer reagent contains, for example, sulfur dioxide, iodine and a base such as pyridine or a pyridine substitute, such as imidazole, ethanolamine, morpholine, guanidine or other amine bases, in a suitable solvent, which can also be the solvent of this invention.

Unless indicated otherwise herein, all details of the Karl Fischer process are fully conventional as described in Angew. Chemie 48, 394 (1935).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLE 1

Preparation of a solvent composition 105 g (0.5 mol) of tetraethylammonium bromide is dissolved in 1 liter of ethylene glycol monomethyl ether, with stirring.

EXAMPLE 2

Determination of water in benzaldehyde

Qualitative comparison of titration in methanol and in the solvent prepared according to Example 1 is carried out:

20 ml of the solvent is initially introduced into the titration vessel of an automatic Karl Fischer apparatus, and is titrated to the end point with Karl Fischer reagent. Using a pipette, 5 ml of benzaldehyde is added, and titration is again carried out. The apparatus switches off after about 3 minutes and indicates that 1.78 ml of Karl Fischer solution has been consumed. The experiment is repeated in the same manner using methanol as solvent. The apparatus has not switched off even after 10 minutes. At this time, the amount of Karl Fischer solution consumed is 14.49 ml.

EXAMPLE 3

Range of application of the solvent of this invention

A number of aldehydes and ketones are titrated in the solvent composition as prepared in Example 1, under conditions analogous to those in Example 2. 10 mg of water are added in each instance, and this is titrated immediately and after 5 minutes. The following amounts of the aldehydes and ketones shown below can be titrated satisfactorily without interference by the formation of acetal or ketal or bisulfite addition:

| Aldehydes | |
| --- | --- |
| Acetaldehyde | 1 ml |
| Propionaldehyde | 1 ml |
| Isobutyraldehyde | 10 ml |
| Crotonaldehyde | 2.5 ml |
| Benzaldehyde | 5 ml |
| Salicylaldehyde | 2 ml |
| 2-Bromobenzaldehyde | 1 ml |
| 3-Anisaldehyde | 2 ml |
| Ketones | |
| Acetone | 10 ml |
| Ethyl methyl ketone | 10 ml |
| Methyl isobutyl ketone | 10 ml |
| 3-Octanone | 10 ml |
| Acetophenone | 10 ml |
| Benzophenone | 5 g |
| 2-Pyrrolidone | 10 ml |
| Acetylacetone | 10 ml |
| Ethyl acetoacetate | 10 ml |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a method for the determination of water in a sample by the Karl Fischer method comprising carrying out a Karl Fischer titration in a Karl Fischer solvent, the improvement wherein said solvent is a solvent composition consisting essentially of a monoalkyl ether of an ethylene glycol and a tetraalkylated ammonium salt which together are effective for use as a Karl Fischer solvent.

2. A method according to claim 1, wherein said solvent composition contains 0.1 to 0.8 mole of said tetraalkylammonium salt per liter of said monoalkyl ether of an ethylene glycol.

3. A method according to claim 1, wherein said solvent composition contains about 0.5 mole of said tetraalkylammonium salt per liter of said monoalkyl ether of an ethylene glycol.

4. A method according to claim 1, wherein the salt is tetraethyl ammonium bromide.

5. A method according to claim 1, wherein the sample comprises an aldehyde, a ketone or a mixture thereof.

6. A method according to claim 1, wherein the tetraalkylated ammonium salt in the solvent composition is not tetrabutylammonium iodide.

7. A method according to claim 1, wherein the anion of the tetraalkylated ammonium salt of the solvent composition is sulfate, nitrate, acetate, thiocyanate, fluoride, chloride or bromide.

8. A method according to claim 1, wherein the alkyl groups of the tetraalkylated ammonium salt are the same or different and each is of 1-6 carbon atoms.

9. A method according to claim 7 wherein the tetraalkylated ammonium salt is a tetramethyl ammonium, tetraethyl ammonium or tetrapropyl ammonium salt.

10. A method according to claim 9, wherein the tetraalkylated ammonium salt is a tetraethyl ammonium salt.

11. A method according to claim 1 wherein said monoalkyl ether of an ethylene glycol is an ethylene glycol monoalkyl ether having an alkyl group of 1-8 carbon atoms or a $C_{1-8}$- monoalkyl ether of diethylene or triethylene glycol.

12. A method according to claim 11, wherein the alkyl groups of the tetraalkylated ammonium salt are the same or different and each is of 1-6 carbon atoms.

13. A method according to claim 12, wherein the anion of the tetraalkylated ammonium salt is a halide, sulfate, nitrate, acetate, or thiocyanate.

14. A method according to claim 11, wherein the ethylene glycol monoalkyl ether is ethylene glycol monomethyl or ethylene glycol monoethyl ether.

15. A method according to claim 14, wherein the salt is tetraethyl ammonium bromide.

16. A method according to claim 15, wherein said solvent composition contains 0.1 to 0.8 mole of said tetraalkyl ammonium bromide per liter of said ethylene glycol monoalkyl ether.

17. A method according to claim 1, wherein the anion of the tetraalkylated ammonium salt is a halide, sulfate, nitrate, acetate, or thiocyanate.

18. A method according to claim 17, wherein the anion is a halide.

19. A method according to claim 18, wherein said halide is a flouride, chloride, bromide or iodide.

20. A method according to claim 19, wherein the halide is a bromide.

21. A method according to claim 20, wherein said solvent composition contains 0.01 to 1 mole of said tetraalkylammonium salt per liter of said monoalkyl ether of an ethylene glycol.

22. A composition useful for the determination of water by the Karl Fischer method, comprising a monoalkyl ether of an ethylene glycol, a tetraalkylated ammonium salt and sulfur dioxide.

23. A composition according to claim 22 comprising 0.01 to 1 mole of a tetraalkyammonium salt per liter of a monoalkyl ether of an ethylene glycol.

24. A composition according to claim 22, further comprising iodine.

25. A composition according to claim 22, further comprising an amine base.

26. A composition according to claim 25, wherein said amine base is selected from the group consisting of pyridine, imidazole, ethanolamine and morpholine.

* * * * *